US008585402B2

(12) United States Patent
Vogel et al.

(10) Patent No.: US 8,585,402 B2
(45) Date of Patent: Nov. 19, 2013

(54) DENTAL DRILL GUIDE SYSTEM

(75) Inventors: Tyson K. Vogel, San Diego, CA (US); Shahram Shaun Zamani, San Diego, CA (US); Sean B. Cahill, Temecula, CA (US); Suneel Ranga Sai Battula, San Diego, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 252 days.

(21) Appl. No.: 12/548,195

(22) Filed: Aug. 26, 2009

(65) Prior Publication Data

US 2010/0173259 A1 Jul. 8, 2010

Related U.S. Application Data

(60) Provisional application No. 61/092,900, filed on Aug. 29, 2008.

(51) Int. Cl.
*A61C 19/04* (2006.01)
(52) U.S. Cl.
USPC .......................................................... 433/72
(58) Field of Classification Search
USPC ............. 433/72–76; 606/80, 96, 60; 269/3, 6
See application file for complete search history.

(56) References Cited

U.S. PATENT DOCUMENTS

| 5,320,529 | A | 6/1994 | Pompa |
| 5,768,134 | A | 6/1998 | Swaelens et al. |
| 5,833,693 | A * | 11/1998 | Abrahami .................. 606/96 |
| 5,888,065 | A * | 3/1999 | Sussman .................... 433/76 |
| 6,537,067 | B1 * | 3/2003 | Wennemann ............... 433/76 |
| 6,869,282 | B2 * | 3/2005 | Carmichael et al. ....... 433/76 |
| 7,331,786 | B2 | 2/2008 | Poirier |
| 7,824,181 | B2 * | 11/2010 | Sers .......................... 433/76 |
| 2004/0172035 | A1 * | 9/2004 | Parmigiani ............... 606/80 |
| 2004/0210229 | A1 * | 10/2004 | Meller ...................... 606/80 |

(Continued)

FOREIGN PATENT DOCUMENTS

| CA | 2657387 A1 | 1/2008 |
| EP | 0528616 A1 | 2/1993 |
| WO | WO2004/075771 A1 | 9/2004 |
| WO | WO2006/130067 A1 | 12/2006 |

(Continued)

OTHER PUBLICATIONS

International Search Report and Written Opinion mailed Dec. 9, 2009 from the International Searching Authority.

*Primary Examiner* — Cris L Rodriguez
*Assistant Examiner* — Mirayda A Aponte
(74) *Attorney, Agent, or Firm* — Schwegman, Lundberg & Woessner P.A.

(57) ABSTRACT

A dental drill guide system, including a handpiece guide which interfaces with a custom surgical guide. The custom surgical guide may be designed based on patient-specific data, such as medical images, for example, and fits conformingly over at least a portion of the patient's dentition at the implant site. The handpiece guide is attachable to an existing dental handpiece, and includes a guide protrusion that interfaces with a guide receptacle of the surgical guide to position and guide the movement of the drill along a desired trajectory. The guide receptacle may have a curved shape to allow for varying the position of the handpiece to aid surgeon access in the drilling procedure.

12 Claims, 8 Drawing Sheets

(56) References Cited

U.S. PATENT DOCUMENTS

| | | | |
|---|---|---|---|
| 2005/0136374 A1* | 6/2005 | Carmichael et al. | 433/76 |
| 2005/0170311 A1 | 8/2005 | Tardieu et al. | |
| 2006/0093988 A1* | 5/2006 | Swaelens et al. | 433/76 |
| 2009/0004625 A1 | 1/2009 | Esposti et al. | |
| 2010/0047737 A1* | 2/2010 | Richard | 433/75 |
| 2010/0151411 A1* | 6/2010 | Suter et al. | 433/75 |
| 2010/0185201 A1* | 7/2010 | Kim | 606/80 |
| 2010/0297574 A1* | 11/2010 | Llop et al. | 433/75 |

FOREIGN PATENT DOCUMENTS

| | | |
|---|---|---|
| WO | WO2007/077223 A1 | 7/2007 |
| WO | WO 2007104842 A1 * | 9/2007 |
| WO | WO2008/006802 A1 | 1/2008 |
| WO | WO2009/004526 A2 | 1/2009 |
| WO | WO2009/034788 A1 | 3/2009 |

* cited by examiner

FIG_1

FIG_2

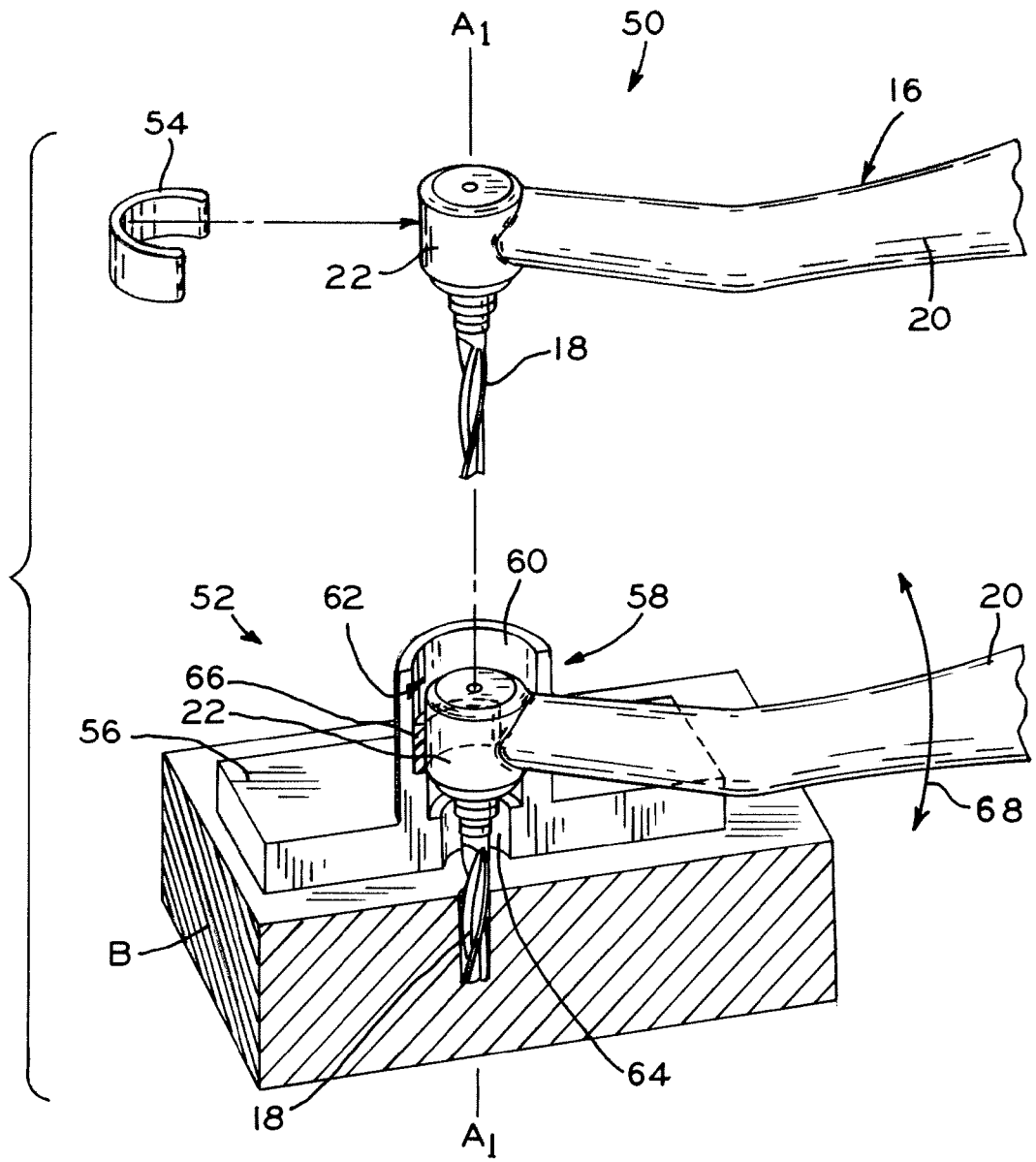
FIG_5

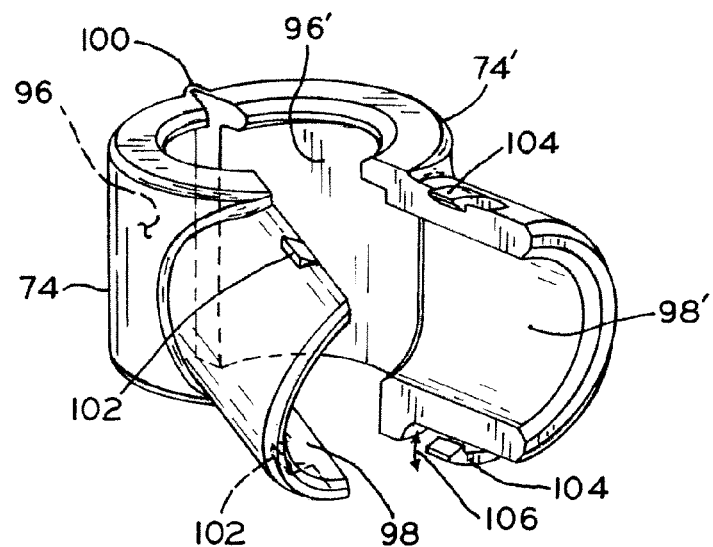
FIG_7
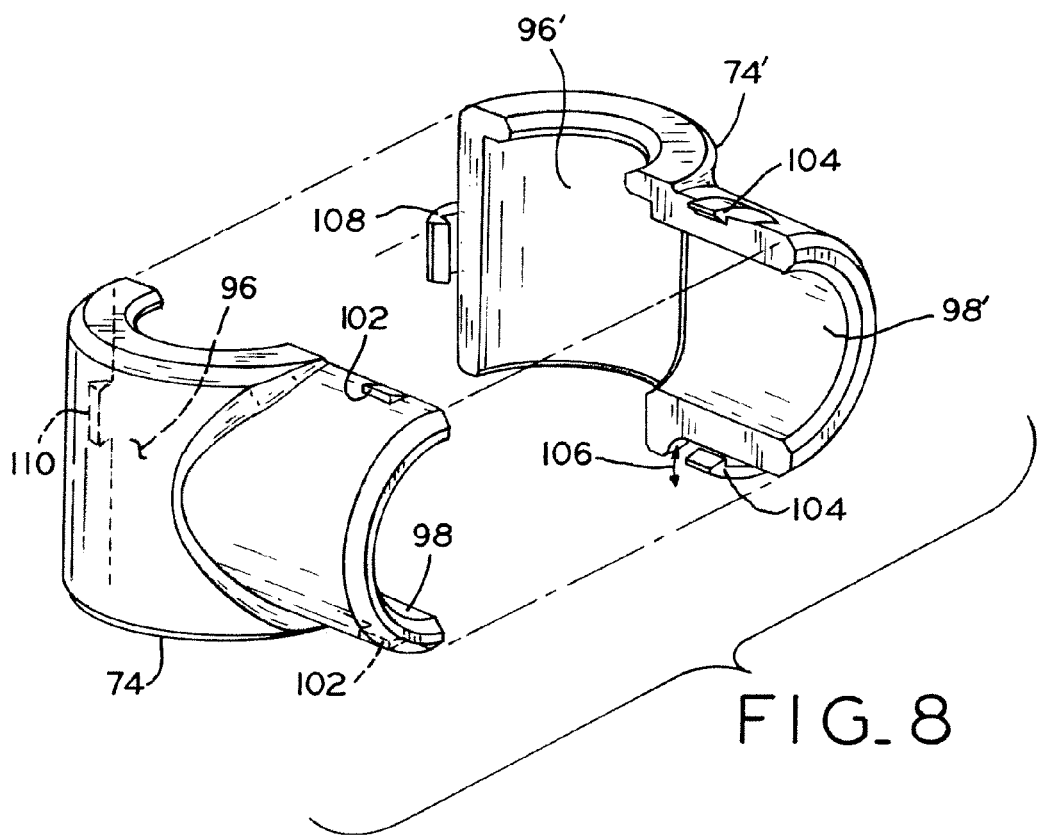
FIG_8

DENTAL DRILL GUIDE SYSTEM

CROSS-REFERENCE TO RELATED APPLICATION

This application claims the benefit under Title 35, U.S.C. §119(e) of U.S. Provisional Patent Application Ser. No. 61/092,900 entitled DENTAL DRILL GUIDE SYSTEM, filed Aug. 29, 2008, the disclosure of which is hereby expressly incorporated herein by reference in its entirety.

BACKGROUND OF THE INVENTION

1. Field of the Invention

The present invention relates to a dental drill guide system and, in particular, relates to a dental drill guide system including a handpiece guide that interfaces with a custom or patient-specific surgical guide.

2. Description of the Related Art

Dental implants are commonly used as anchoring members in prosthodontic restorations to provide prosthetic teeth at one or more edentulous sites in a patient's dentition at which the patient's original natural teeth have been lost or damaged. Typically, known implant systems include a dental implant made from a suitable biocompatible material, such as titanium. The dental implant is typically threaded into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods to replicate the shape of the tooth being replaced.

Many dental implant surgeries are performed in two stages. In the initial or first stage, an incision is made in the patient's gingiva at an edentulous site, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around and/or into the implant to securely anchor the implant in the surrounding bone, a process known as osseointegration.

In a second stage of the procedure following osseointegration, the dentist surgically reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example.

If the patient has more than one tooth missing, multiple implants may be used to provide anchorage for a denture bar, a bridge, or other prosthodontic appliance.

To drill holes in the jawbone of a patient, an oral surgeon may use a drill guide, which is typically formed as a custom patient-specific appliance that overlays the drill site and at least a portion of the surrounding gum tissue and/or dentition. The drill guide includes a hole aligned along the intended drill axis, and one or more removable drill guide tubes may be positioned within the drill guide hole to allow drills of different diameters to be used in succession for drilling the holes in the jawbone in which the implants will be secured.

What is needed is a method that is an improvement on the foregoing.

SUMMARY OF THE INVENTION

The present invention provides a dental drill guide system, including a handpiece guide which interfaces with a custom patient-specific surgical guide. The custom surgical guide may be designed based on patient-specific data, such as medical images, for example, and fits conformingly over at least a portion of the patient's dentition at the implant site. The handpiece guide is attachable to an existing dental handpiece and, in one embodiment, includes a guide post that interfaces with a guide receptacle of the surgical guide to position and guide the movement of the drill along a desired trajectory. The guide receptacle may have an arcuate or curved shape to allow for varying the position of the handpiece to aid surgeon access in the drilling procedure.

In one embodiment, a dental drill guide system for use with an existing dental handpiece includes a base adapted to fit conformingly over at least a portion of a patient's dentition and a handpiece guide attachable to the dental handpiece. The base includes a partially cylindrical portion concentric with an implant axis. The handpiece guide is engageable with the partially cylindrical portion to substantially align a drill axis of the handpiece with the implant axis.

In one aspect, the partially cylindrical portion of the dental drill guide system includes an arcuate-shaped guide slot, and the handpiece guide includes a guide post engageable within the guide slot.

In another aspect, the guide post of the handpiece guide is aligned parallel to, and offset with respect to, the drill axis. The handpiece is rotatable about the drill axis when the handpiece guide is engaged with the guide slot.

In another aspect, the arcuate-shaped slot defines a first endpoint and a second endpoint defining an angle formed between the first endpoint and the second endpoint with a vertex at the drill axis. The handpiece guide is rotatable through an angular range of motion equal to the angle when the guide post is engaged within the guide slot.

In yet another aspect, the dental drill guide system includes a bushing having an axis aligned with the implant axis. The bushing is dimensioned to receive the drill.

In still another aspect, the partially cylindrical portion defines a guide receptacle with a lateral opening and a stop wall. The handpiece guide is receivable within the guide receptacle and engageable with the stop wall to limit a drill depth of the handpiece. The handpiece guide may be a curved, partially annular member. Alternatively, the handpiece guide may have first and second handpiece guide portions fittable to one another about at least a portion of the handpiece.

In another embodiment, a dental drill guide system for use with an existing dental handpiece includes a base adapted to fit conformingly over at least a portion of a patient's dentition and a handpiece guide attachable to the dental handpiece. The base includes a surgical guide with a guide receptacle, the guide receptacle including an arcuate-shaped guide slot. The handpiece guide includes a guide post engageable with the guide slot.

In one aspect, the dental drill guide system includes a drill defining a drill axis and the guide post of the handpiece guide is aligned parallel to, and offset with respect to, the drill axis. The handpiece is rotatable about the drill axis when the handpiece guide is engaged with the guide slot.

In another aspect, the arcuate-shaped slot has a first endpoint and a second endpoint defining an angle formed between the first endpoint and the second endpoint with respect to the drill axis. The handpiece guide is rotatable through an angular range of motion equal to the angle when the guide post is engaged with the guide slot.

In yet another aspect, the surgical guide includes at least one bushing having an axis that is alignable with the drill axis. The bushing is sized to cooperate with the drill. The bushing constrains lateral translation of the drill axis when the drill is engaged with the bushing. The bushing may be removably received within the base of the drill guide.

In a third embodiment, a dental drill guide system for use with an existing dental handpiece includes a surgical guide and a handpiece guide attachable to the dental handpiece. The surgical guide includes a substantially semi-cylindrically shaped guide receptacle having a lateral opening and a stop wall. The handpiece guide is receivable within the guide receptacle and engageable with the stop wall to limit a drill depth of the dental handpiece.

In one aspect, the dental drill guide system includes a drill with a drill axis. The guide receptacle has a guide axis, and the drill axis is substantially aligned with the guide axis when the handpiece guide is received within the guide receptacle.

In another aspect, the handpiece guide comprises a curved, partially annular member.

In yet another aspect, the handpiece guide may include a first handpiece guide portion and a second handpiece guide portion, with the handpiece guide being shaped to cooperate with the dental handpiece to limit a drill depth of the handpiece. The first handpiece guide portion may have a locking mechanism with a female clip portion and a male clip portion adapted to cooperate with the female clip portion to couple the first handpiece guide portion with the second handpiece guide portion. The handpiece guide may also include a hinge rotatably joining the first handpiece guide portion and the second handpiece guide portion.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawing, wherein:

FIG. 5 is an exploded schematic view showing components of a dental drill guide system according to another embodiment of the present invention, including a handpiece guide attachable to a handpiece, and a custom surgical guide;

FIG. 7 is a perspective view illustrating the handpiece guide shown in FIG. 5, with a hinge attachment attaching the handpiece guide members;

FIG. 8 is a perspective view of the handpiece guide shown in FIG. 6, illustrating a clip type attachment structures on each of the handpiece guide.

Figure 1:
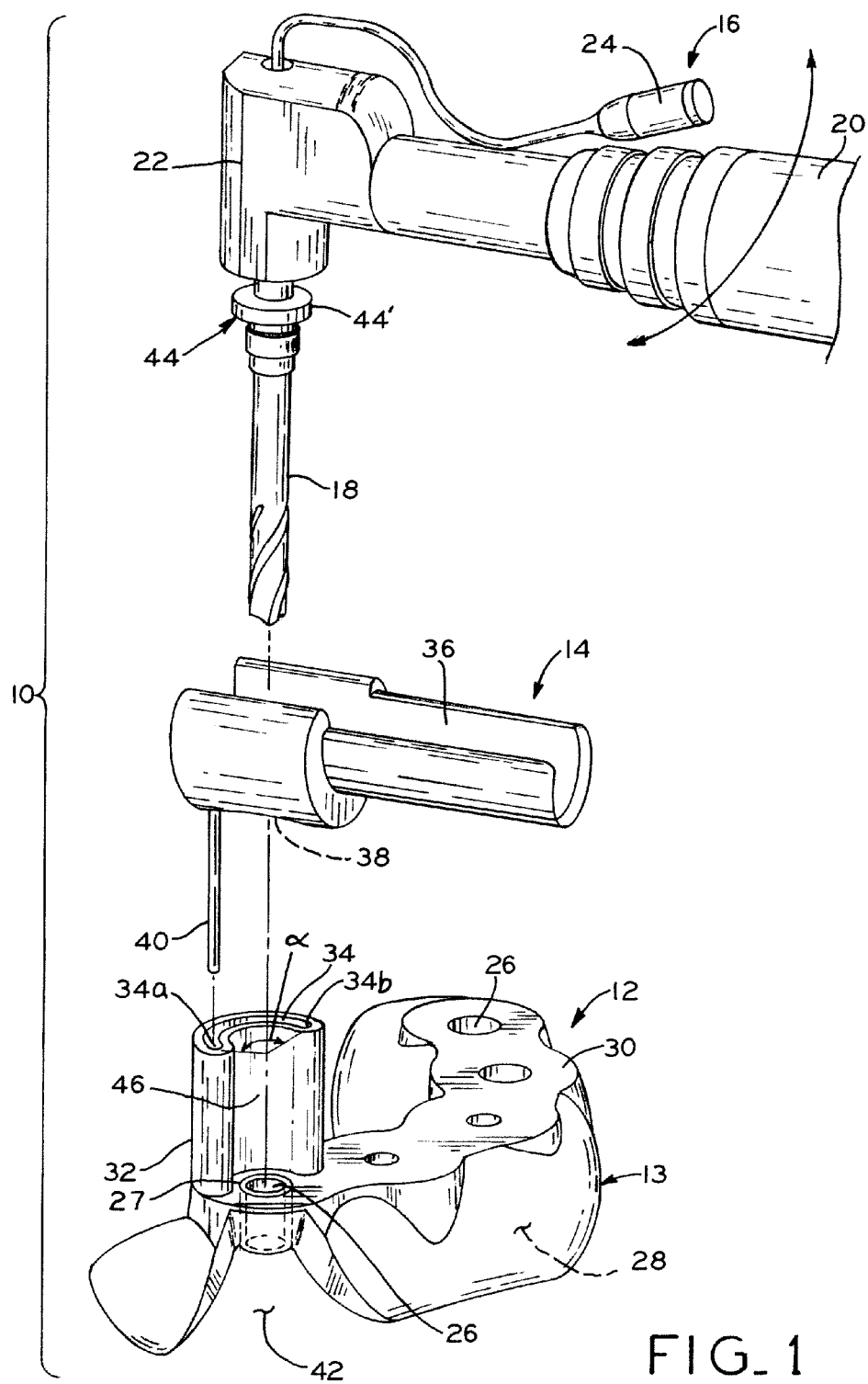
FIG. 1 is an exploded view of components of a dental drill guide system in accordance with a first embodiment of the present invention, including a custom surgical guide, a handpiece guide, and a handpiece with a drill.

Corresponding reference characters indicate corresponding parts throughout the several views. Although the exemplifications set out herein illustrate embodiments of the invention, in several forms, the embodiments disclosed below are not intended to be exhaustive or to be construed as limiting the scope of the invention to the precise forms disclosed.

DETAILED DESCRIPTION

Referring to FIG. 1, the principal components of a dental drill guide system 10 according to a first embodiment of the present invention are shown. Dental drill guide system 10 generally includes custom surgical guide 12 and handpiece guide 14, and is used in combination with an existing dental handpiece 16 and a series of drills 18. Handpiece 16 may be of any type available from many commercial sources, and is used with a series of drills 18 having increasing diameters for the progressive drilling of one or more holes in the jawbone of a patient for dental implant(s). Handpiece 16 generally includes handle portion 20, head portion 22 having a rotational drive mechanism (not shown) and a chuck structure for interfacing with drill(s) 18, and water irrigation assembly 24.

Surgical guide 12 may be designed and manufactured based on patient-specific data, such as patient images taken via an imaging modality such as CT, MRI, or any other imaging modality. Once the patient's dentition is scanned with the imaging modality, the medical image may be segmented to form a computer model of the patient's dentition, which then may be used to plan the orientation and position of one or more implants in the patient's mandible and/or maxilla with respect to the patient's surrounding dental anatomy. After the implants have been placed into the dental model, the dental model may be used to design a custom surgical guide 12 which is adapted to fit conformingly around the patient's teeth and/or gums or bone surrounding the implant site, and which includes a hole 26 aligned along the desired trajectory of the implant. The custom surgical guide may optionally include more than one hole 26 if more than one implant is to be used. One exemplary method for designing a custom surgical guide is disclosed in U.S. Pat. No. 5,768,134 to Swaelens et al., the disclosure of which is expressly incorporated herein by reference. The surgical guide may then be manufactured from a suitable material, such as a metal or hard plastic, by molding, casting, or milling, or via a rapid prototyping process such as stereolithography.

Figure 2:
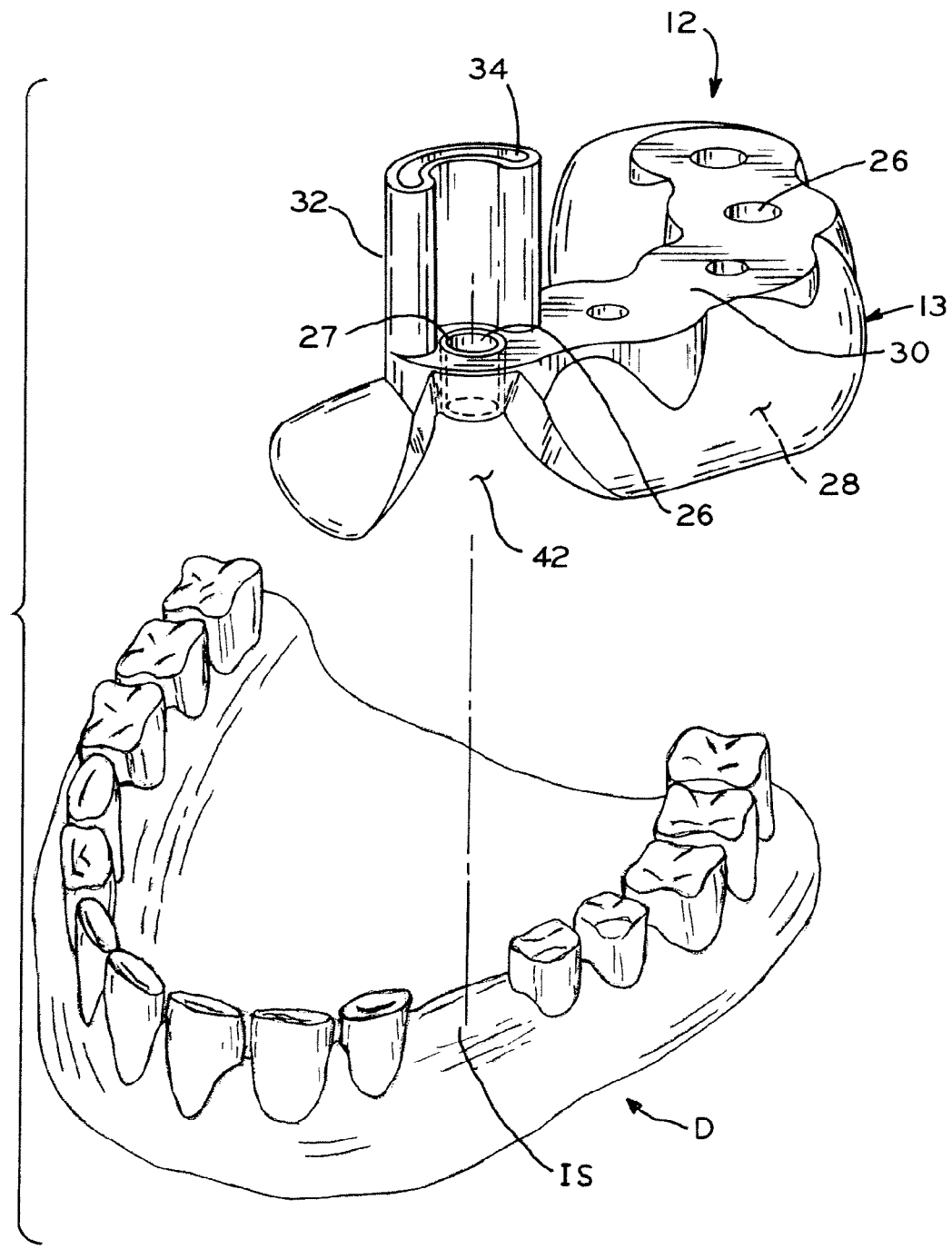
FIG. 2 is an exploded view showing a portion of a patient's dentition and the custom surgical guide.
Figure 3:
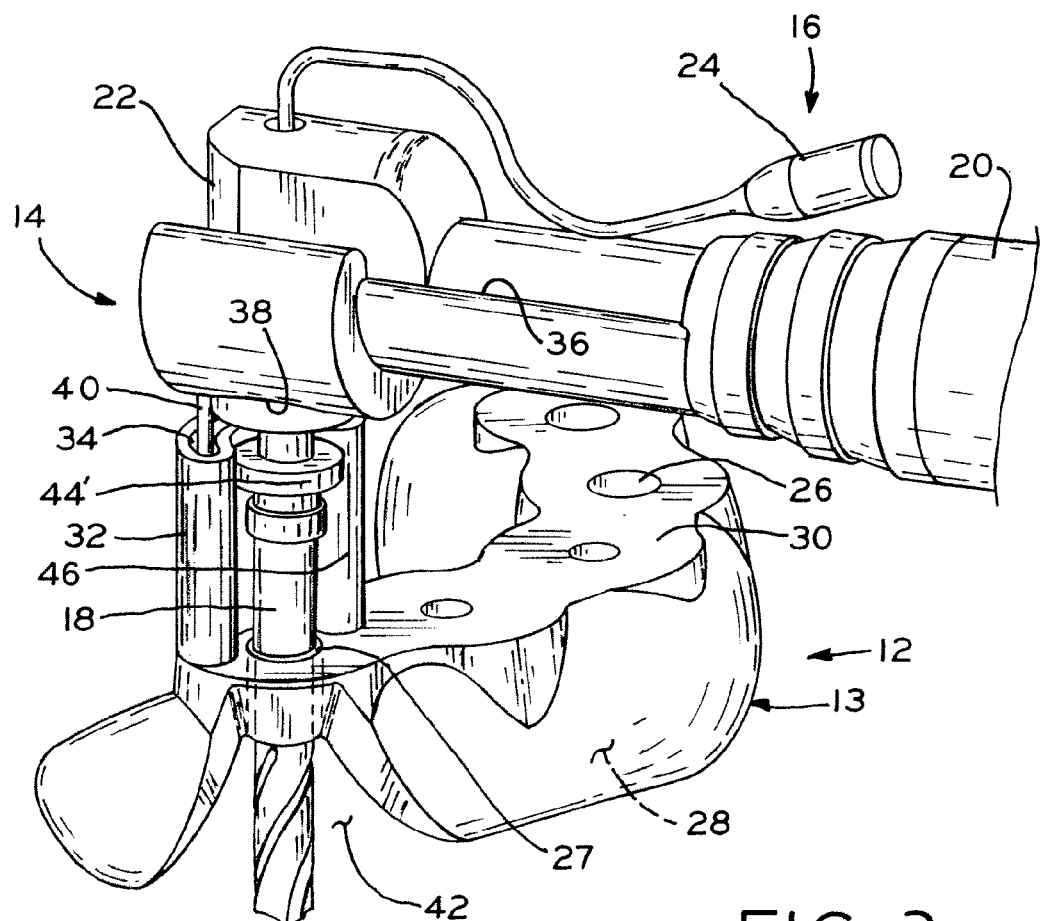
FIG. 3 is a perspective view showing use of the handpiece to drill a hole in a jawbone using the custom surgical guide and the handpiece guide.

The surgical guide 12 is shaped to include a base 13 having a first side 28, shown herein as a lower surface when surgical guide 12 is used with the mandible, that conforms to at least a portion of the teeth and gums that surround the implant site to locate the surgical guide 12 over the patient's dentition "D" as shown in FIG. 2. Base 13 of surgical guide 12 also includes an opposite second side 30, shown herein as an upper side when surgical guide 12 is used with the mandible, which includes a guide receptacle 32 formed as a projection from the second side 30 and having an arc-shaped guide slot 34 having endpoints 34(*a*) and 34(*b*). As shown in FIGS. 1 and 2, the guide receptacle 32 and its guide slot 34 extends around at least a portion of the circumference of the guide hole 26 of the surgical guide 12, such that guide slot 34 is formed concentrically with guide hole 26. Optionally, guide hole 26 may include a bushing or sleeve element 27 therein that may be made of a different material from the remainder of surgical guide 12. For example, a guide bushing or sleeve 27 made of a metal or hard plastic material may be embedded within surgical guide 12, as shown in FIGS. 1-3. Also, surgical guide 12 may include multiple holes 26, and multiple corresponding guide receptacles 32, for locating multiple implants within a patient's dentition.

Handpiece guide 14 may be custom designed in combination with surgical guide 12, or alternatively, may be a separate, pre-existing component. Handpiece guide 14 includes a suitable handpiece interface structure adapted to connect handpiece guide 14 with head portion 22 of handpiece 16, such as a snap fit, press fit or other type of connection mechanism. Handpiece guide 14 may be designed based on an existing dental handpiece 16, and therefore the shape and/or handpiece interface structure of handpiece guide 14 may vary depending upon the particular existing handpiece 16 to be used. As shown in FIG. 1, handpiece guide 14 may be made of a somewhat rigid plastic material, and includes a channel 36 adapted to be snap fit around handle portion 20 and/or head portion 22 of handpiece 16. Handpiece guide 14 also includes an opening 38 coaxial with drill 18 of handpiece 16 having a larger diameter than drill 18 such that drill 18 may pass through opening 38 and different drills 18 of varying diameter may be used with handpiece 16. Handpiece guide 14 further includes a guide post 40 projecting therefrom which is aligned parallel with, and offset with respect to, drill 18 and the drill axis, and is receivable within guide slot 34 of guide receptacle 32 of surgical guide 12.

In use, after the patient's jawbone has been exposed by incising a portion of the gum tissue, for example, surgical guide 12 is fitted conformingly to the patient's dentition with hole 26 located over the implant site "IS" as shown in FIG. 2, and handpiece guide 14 is fitted to an existing handpiece 16. A first drill 18 is fitted to the chuck structure of head portion 22 of handpiece 16, and will typically have a relatively smaller diameter for drilling a relatively small pilot hole in the patient's jawbone. Guide post 40 of handpiece guide 14 is fitted within guide slot 34 of guide receptacle 32 of the surgical guide 12, wherein guide post 40 extends parallel to the axis of drill 18 and therefore extends parallel to the trajectory defined by guide hole 26 in surgical guide 12 which corresponds to the trajectory of the implant (not shown) that will be implanted within the patient's jawbone. The engagement of guide post 40 within guide receptacle 34 therefore orients handpiece 14 and drill 18 drill during drilling and, when handpiece guide 14 bottoms out against the top of guide receptacle 32, the depth of drill 18 and the hole formed by drill 18 is limited, which depth may be varied as desired based on the design of surgical guide 12 and/or the length of drill 18. Thereafter, the first drill 18 may be replaced with progressively larger drills 18 for enlarging the hole in the patient's jawbone, and finally, handpiece 16 is used to thread a dental implant (not shown) within the patient's jawbone. Optionally, a plurality of guide bushings or sleeves 27 having varying inner diameters corresponding to the diameters of drills 18 may be removably fitted within guide hole 26 of surgical guide 12 to guide drills 18.

Optionally, dental drill guide system 10 may include a drill collar 44 mounted between head portion 22 of handpiece 16 and drill 18. Drill collar 44 has an arcuate outer surface 44' sized to cooperate with an arcuate inner surface 46 of guide receptacle 32, as shown in FIGS. 1 and 3. Drill collar 44 may be vertically oriented with respect to drill 18 and handpiece 16 such that, as guide post 40 is received within guide receptacle 34, arcuate outer surface 44' of drill collar 44 engages with arcuate inner surface 46 of guide receptacle 32 to prevent lateral movement of the axis of drill 18 and to thereby maintain drill 18 on a path coincident with the intended dental implant. Drill collar 44 may be attached to handpiece 16, or to drill 18, for example. Alternatively, drill collar 44 may be attached to handpiece guide 14, such as in a region generally adjacent guide post 40. Collar 44 may be used in addition to, or in lieu of bushing 27 to maintain drill concentricity.

Figure 4A:
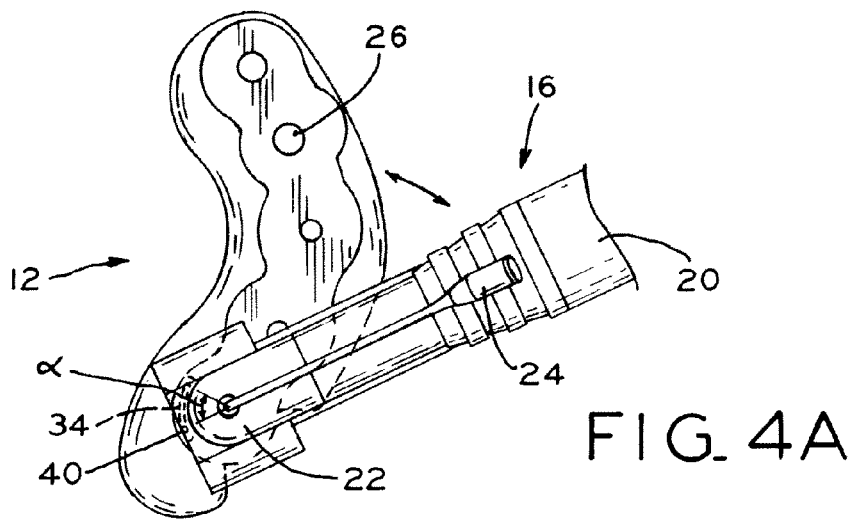
FIG. 4a is a to view of a dentition with a dental handpiece provided in a first position relative to the dentition.
Figure 4B:
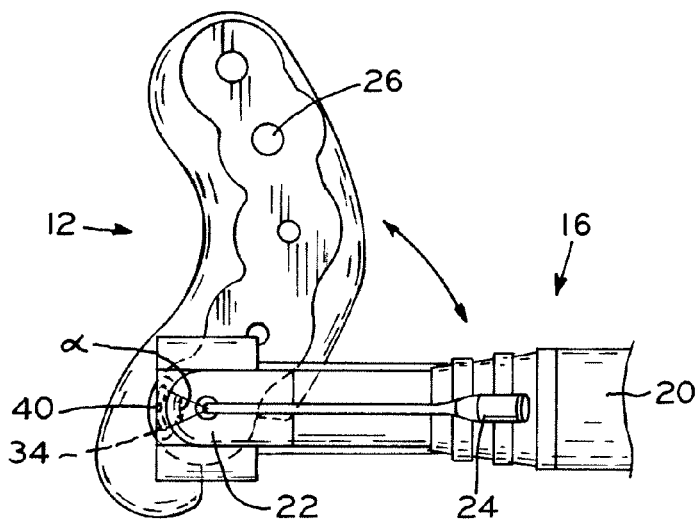
FIG. 4b is a top view of a dentition similar to FIG. 4a but showing the dental handpiece in a second angular position relative to the dentition.
Figure 4C:
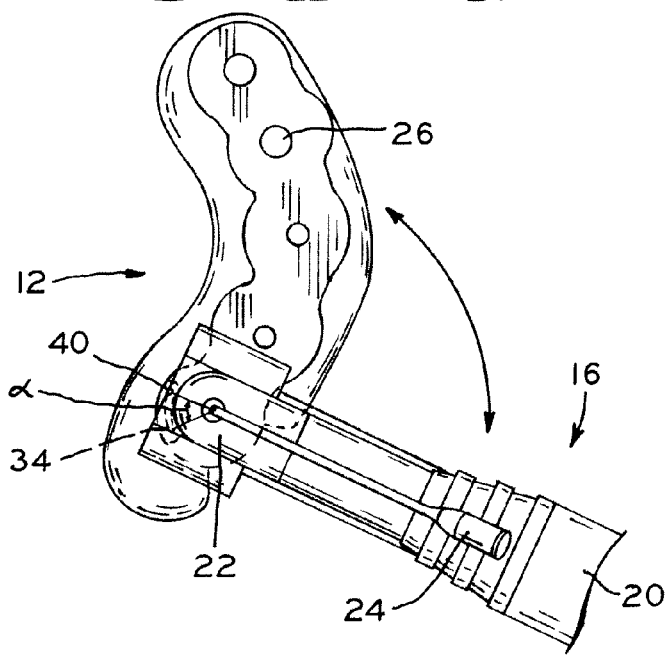
FIG. 4c is a top plan view similar to FIG. 4a but with the dental handpiece in yet another angular disposition relative to the dentition.

Guide slot 34 spans an angular range between endpoints 34(*a*), 34(*b*) with the drilling axis as the vertex. Advantageously, as may be seen in FIGS. 4A-C, the arcuate shape of guide slot 34 in which guide post 40 is received allows handpiece 16 to be pivoted about an angle α equal to the angular range of guide slot 34, either before or during drilling, within a plane generally perpendicular to the axis of drill, thereby allowing easier access by the surgeon to the implant site within the mouth of the patient. Guide slot 34 may be configured to allow handpiece 16 may be rotated through a range of motion that may be as little as 25°, 45° or 75° and as much as 135°, 180° or 200°, or within any of the foregoing ranges.

Optionally, as shown in FIG. 1, surgical guide may include a window or cut away portion 42, proximate guide hole 26 of surgical guide 12 which allows for better observation of the drilling site by the surgeon. Further, cut away portion 42 may provide a better fit of surgical guide 12 about the implant site by providing clearance from the gums in the event that the patient's gums swell due to numbing during surgery. Also, although guide receptacle 32 is shown in the present embodiment as extending from second side 30 of drill guide 12, guide receptacle 32 may also be located inwardly, or lingually, on the lingual side of drill guide 12 in order to reduce the height of guide receptacle 32.

Referring to FIG. 5, a drill guide system is shown according to another embodiment of the present invention. Drill guide system 50 generally includes custom surgical guide 52 and handpiece guide, or depth stop, 54.

Custom surgical guide 52 may be custom made in the manner described above with respect to surgical guide 12, and generally includes a base wall 56 having a profile that is conformed to fit over the bone "B" of a patient's jaw at the implant site. Base wall 56 provides a location for surgical guide 52 (shown schematically in FIG. 5), and may also be custom shaped or patient-specific to overlay the patient's gum tissue and/or the teeth of the patient's dentition that are adjacent to the implant site in order to provide a conforming, custom fit surface corresponding to a patient's dentition. Surgical guide 52 additionally includes guide receptacle 58 which is formed with a semi-cylindrical or partially cylindrical wall 60 about an axis $A_1$-$A_1$ which conforms to the desired implant orientation. Semi-cylindrical wall 60 of guide receptacle 58 also defines an access opening 62 through which handpiece 16 may be inserted as described below. Guide receptacle 58 also includes a drill opening 64 through base wall 56 through which drills 18 of handpiece 16 and the implant (not shown) may pass. A semi-annular stop wall 66 is formed within guide receptacle 58 that has a reduced inner diameter as compared to semi-cylindrical wall 60 of guide receptacle 58. Stop wall 66 limits the drill depth, as described below.

Handpiece guide 54 may be formed of a semi-rigid plastic material or metal, and is configured for a snap-fitting attachment to head portion 22 of handpiece 16. Handpiece guide 54 may be formed as a curved, partially annular member that is shaped for snap-fitting around head portion 22 of handpiece 16, and may be custom-designed to include a key or interface structure similar to that of handpiece guide 14 described above for securing the location of handpiece guide 54 with respect to the head portion 22 of the particular existing handpiece 16 that is used. In addition to securing handpiece guide 54 to head portion 22, the interface structure may also operate to prevent handpiece guide 54 from moving or translating axially, i.e., along axis $A_1$-$A_1$ or the drill axis. For example, a key or lip or protuberance may cooperate with a portion of head portion 22 to couple and axially fix handpiece guide 54 to head portion 22. Thus, when handpiece guide 54 contacts stop wall 66, the interface structure may prevent further axial motion of head portion 22 toward dentition "D".

In use, after handpiece guide 54 is attached to handpiece 16, handpiece 16 and its drill 18 are inserted within guide receptacle 58 either axially, i.e., along axis $A_1$-$A_1$, or alternatively, from a lateral direction through access opening 62, which advantageously eases the insertion of handpiece 16 into surgical guide 52.

Thereafter, handpiece guide 54 is brought into engaging contact with the inner surface of semi-cylindrical or partially cylindrical wall 60 of guide receptacle 58 to align drill 18 along axis $A_1$-$A_1$ corresponding to the desired orientation of the implant. Handpiece 16 may be rotated within access opening 62 of guide receptacle 58 as illustrated by arrow 68 to a desired use angle depending upon the location of surgical guide 56 within the patient's dentition. Thus, guide receptacle 58 allows easier access by the surgeon to the implant site within the mouth of the patient.

Advantageously, in this connection, the semi-cylindrical or partially cylindrical shape of guide receptacle 58 allows handpiece 16 to be rotated through an angular range of motion, approaching 180°, while maintaining concentricity of the axis of drill 18 with axis $A_1$-$A_1$. However, it is within the scope of the present invention that handpiece 16 may be rotated within access opening 62 of guide receptacle 58 through a range of motion that may be as little as 25°, 45° or 75° and as much as 135°, 180° or 200°, or within any of the foregoing ranges.

After drill 18 begins drilling a hole in the patient's jaw bone "B" upon movement of handpiece 16 along axis $A_1$-$A_1$, handpiece guide 54 will bottom out against stop wall 66 within guide receptacle 58 to limit the drill depth. Similar to the embodiment discussed above, progressively larger drills 18 may be used to enlarge the hole within the jaw bone "B", followed by the placement of an implant.

Referring now to FIGS. 6-9, the drill guide system is shown according to another embodiment of the present invention. Drill guide system 70 generally includes custom surgical guide 72 and handpiece guide 73 including first and second handpiece guide or depth stop members 74, 74', respectively.

Figure 6:
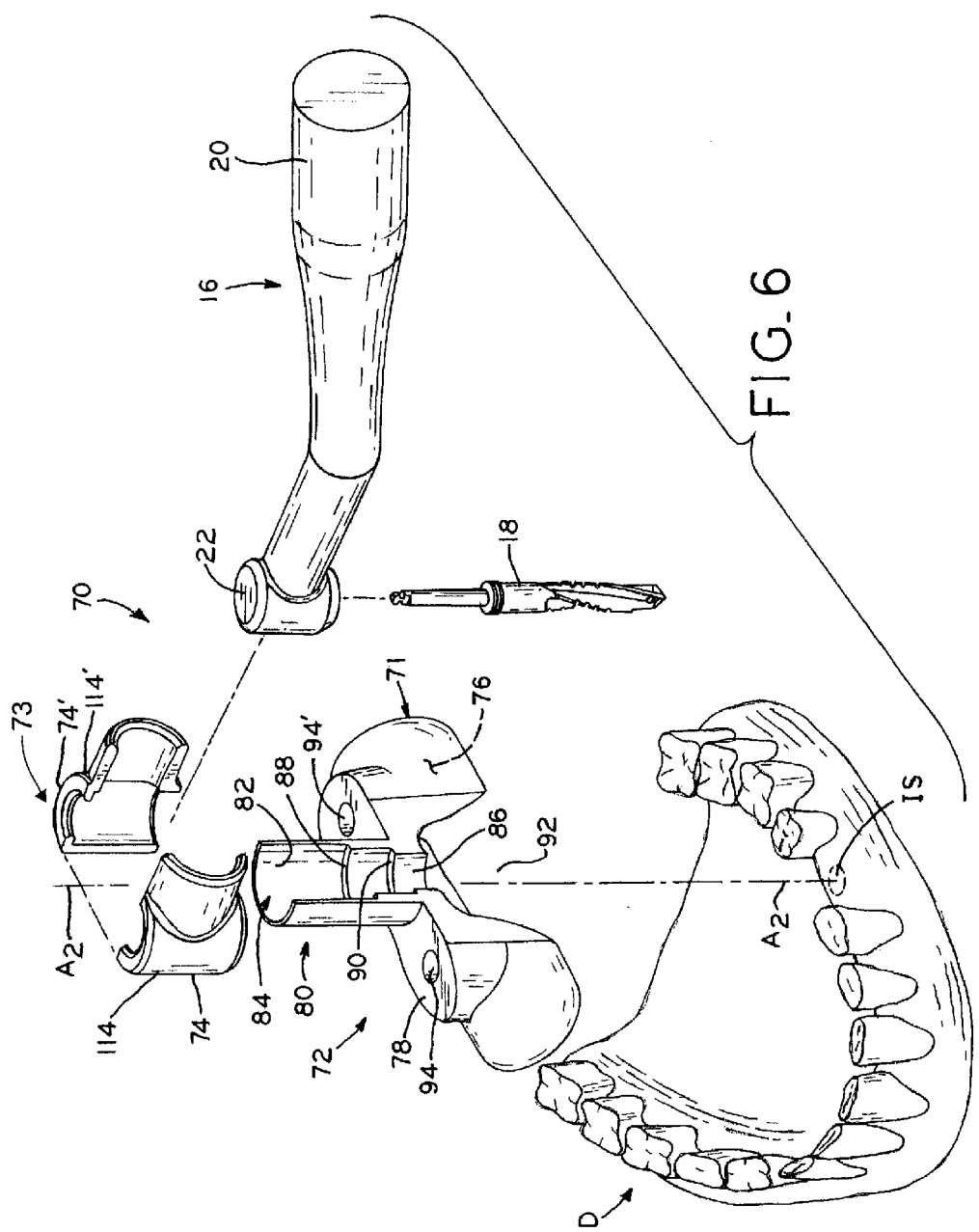
FIG. 6 is an exploded view of components of a dental drill guide system in accordance with yet another embodiment of the present invention, including a handpiece guide comprising two handpiece guide members attachable to a handpiece, and a custom surgical guide.
Figure 9:
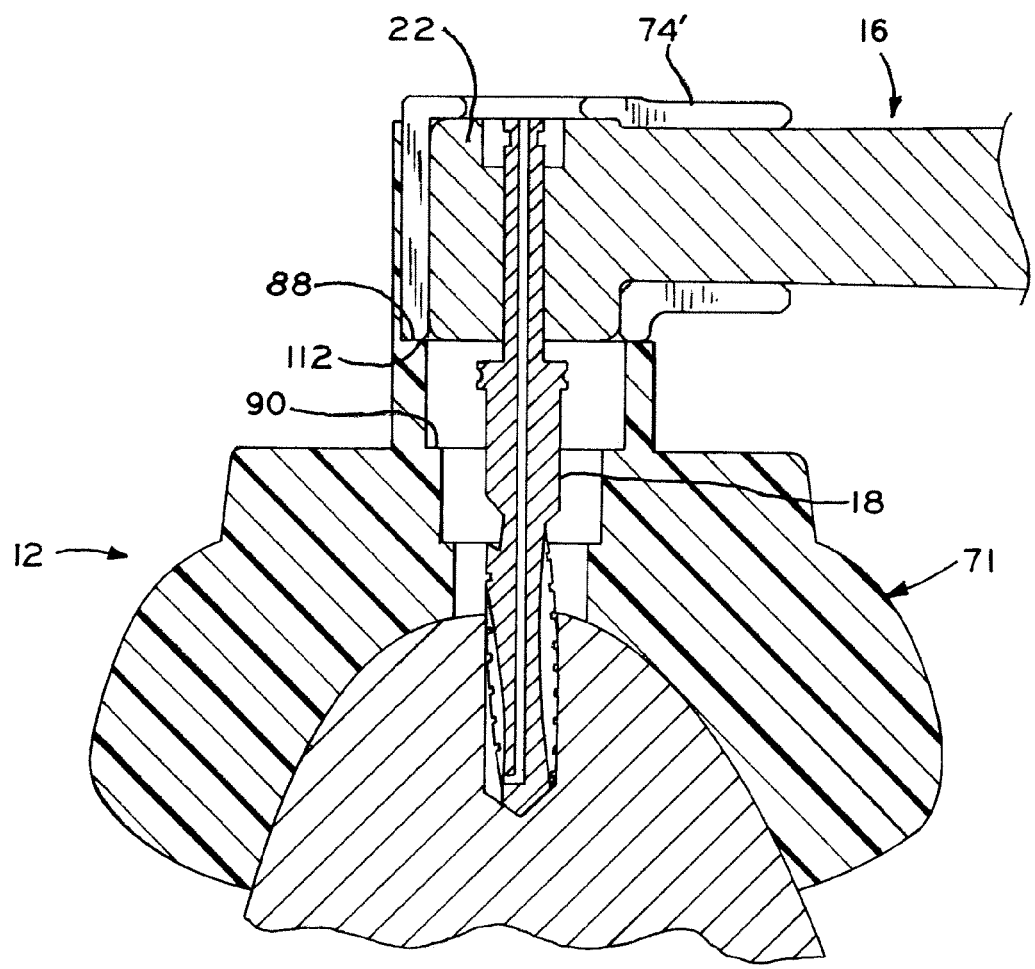
FIG. 9 is a section view of the dental drill guide system shown in FIG. 6 showing use of the handpiece to drill a hole in a jaw bone using the dental drill guide system.

Custom surgical guide 72 may be custom made in the manner described above with respect to surgical guide 12, and is shaped to include a base 71 having a first side 76, shown in FIG. 6 as a lower surface when surgical guide 72 is used with the mandible, that conforms to the teeth and gums that surround the implant site to locate the surgical guide 12 over the patient's dentition "D". Base 71 also includes an opposite second side 78, shown herein as an upper side when surgical guide 12 is used with the mandible, which includes a guide receptacle 80 formed as a projection from the second side 78 and having a semi-cylindrical or partially cylindrical wall 82 about an axis $A_2$-$A_2$ which conforms to the desired implant orientation. Semi-cylindrical wall 82 of guide receptacle 80 also defines an access opening 84 through which handpiece 16 may be inserted as described below. Guide receptacle 80 also includes a drill opening 86 through which drill 18 of handpiece 16 and an implant (not shown) may pass. An upper semi-annular stop wall 88 is formed within guide receptacle 80 and defines a reduced inner diameter relative to semi-cylindrical wall 82. Upper stop wall 88 limits the drill depth when handpiece guide 73 is attached to handpiece 16, as described below. A lower semi-annular stop wall 90 is formed within guide receptacle 80 and defines a reduced inner diameter with respect to both semi-cylindrical wall 82 and upper semi-annular stop wall 88 of guide receptacle 80. Stop wall 90 offers a second, alternative drill guide depth control, as described below. Surgical guide 72 may include multiple guide receptacles 80, such as for multiple endentulous sites in a patient's dentition "D" similar to implant site "IS". For example, additional guides similar to guide 80 may be located at alternative sites 94, 94'.

Optionally, as shown in FIG. 6, surgical guide 72 may include a window or cut away portion 92 proximate guide hole 86 of surgical guide 72 which allows for better observation of the drilling site by the surgeon. Features and benefits of window 92 may be similar to cut away portion 42 shown in FIG. 1 and described above.

Referring now to FIGS. 6-8, first handpiece guide portion 74 and second handpiece guide portion 74' have overall shapes and geometries that are substantial mirror images of one another, with differing structures for their respective attachment mechanisms, as described below. However, it is within the scope of the present invention that first and second handpiece guide portions 74, 74' may be different from one another, or may be substantially identical to one another.

Handpiece guide 73 is configured to conform to a head portion 22 of handpiece 16. More particularly, and as shown in FIGS. 7 and 8, handpiece guide 73 has vertically oriented inner annular surfaces 96, 96', respectively and horizontally oriented inner annular surfaces 98, 98', respectively. Surfaces 96, 96' are shaped to conform to head portion 22, and surfaces 98, 98' are shaped to conform to a portion of handle 20 that is adjacent head portion 22. However, handpiece guide 73 may be custom designed to conform to other handpiece designs and configurations.

In one embodiment, as shown in FIG. 7, first and second handpiece guide portions 74, 74' may be attached to one another by a hinge 100. Hinge 100 allows handpiece guide portions 74, 74' to be rotated relative to one another to an open position, such as shown in FIG. 7, wherein head portion 22 may be inserted. Handpiece guide portions 74, 74' are then rotated to a closed position of handpiece guide 73 in which head portion 22 is in contact with surfaces 96, 96' and a distal portion of handle 20 is in contact with surfaces 98, 98'. In the closed position, handpiece guide 73 is secured to handle 16. To retain handpiece guide 73 in the closed position, the embodiment of FIG. 7 includes a locking mechanism with female clip portions 102 on first handpiece guide portion 74 and male clip portions 104 on second handpiece guide portion 74'. When in the closed position, female clip portions 102 cooperate with male clip portions 104 to secure first handpiece guide portion 74 to second handpiece guide portion 74' and, consequently, to handpiece 16. Male clip portions 104 may be rotated in a direction indicated by arrow 106 to release the lock.

In the embodiment shown in FIG. 8, no hinge is provided. First handpiece guide portion 74 has a female clip portion 110 and second handpiece guide portion 74' has a male clip portion 108 which cooperate in a similar manner to female clip portions 102 and male clip portions 104 to secure handpiece guide portions 74, 74' to one another, as described above.

In use, after handpiece guide 73 is attached to handpiece 16, handpiece 16 and its drill 18 are inserted within guide receptacle 80 either axially, i.e., along axis $A_2$-$A_2$, or alternatively, from a lateral direction through access opening 84, which advantageously eases the insertion of handpiece 16 into surgical guide 80. In particular, when drill guide system 70 is used in a confined space, such as the mouth of a patient, axial insertion of drill 18 into guide receptacle 80 may be impractical or impossible due to space limitations. In this situation, access for drill 18 along a lateral direction through access opening 84 facilitates axial alignment of drill 18 with implant site "IS".

Thereafter, outer surfaces 114, 114' (shown in FIG. 6) of handpiece guide 73 is brought into engaging contact with the inner surface of semi-cylindrical or partially cylindrical wall 82 of guide receptacle 80 to align drill 18 along axis $A_2$-$A_2$ corresponding to the desired orientation of the implant. Handpiece 16 may be rotated within access opening 84 of guide receptacle 80 through a range of motion that may be as little as 25°, 45° or 75° and as much as 135°, 180° or 200°, or within any of the foregoing ranges. As long as outer surfaces 114, 114' are maintained in contact with inner surface of wall 82, substantial concentricity between the axis of drill 18 and axis $A_2$-$A_2$ is maintained.

After drill 18 begins drilling a hole in the patient's jaw bone upon movement of handpiece 16 along axis $A_2$-$A_2$, a bottom surface 112 of handpiece guide 73 will come into contact with upper stop wall 88 within guide receptacle 80 to halt further downward motion of drill 18, thereby limiting the depth of the drill bit. Similar to the embodiment discussed above, progressively larger drills 18 may be used to enlarge the hole within the jaw bone, followed by the placement of an implant at implant site "IS".

A lower stop wall 90 may be provided for an alternate drill depth. The handpiece guide may be altered or added to for engagement with lower stop wall 90, such as by having a downwardly extending portion that will bypass upper stop wall 88 and contact lower stop wall 90, for example.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dental drill guide system for use with an existing dental handpiece, comprising:
   a base adapted to fit conformingly over at least a portion of a patient's dentition, said base including a partially cylindrical portion concentric with an implant axis; and
   a handpiece guide attachable to the dental handpiece, said handpiece guide engageable with said partially cylindrical portion to substantially align a drill axis of the handpiece with the implant axis, wherein said partially cylindrical portion includes an arcuate guide slot of less than 360°, and wherein said partially cylindrical portion defines a guide receptacle having a first diameter and includes a stop wall having a second diameter, the second diameter being reduced relative to the first diameter, at least a portion of the guide receptacle extending outwardly from an outer surface of the base, said handpiece guide being longitudinally receivable within said guide receptacle to guide movement of the handpiece longitudinally along the implant axis, the handpiece guide engageable with said stop wall to limit a drill depth of said handpiece;
   wherein said handpiece guide includes a guide post engageable within said guide slot.

2. The dental drill guide system of claim 1, wherein said guide post of said handpiece guide is aligned parallel to, and offset with respect to, the drill axis, whereby said handpiece is rotatable about the drill axis when said handpiece guide is engaged with said guide slot.

3. The dental drill guide system of claim 1, wherein said arcuate-shaped guide slot defines a first endpoint and a second endpoint defining an angle formed between the first endpoint and the second endpoint with a vertex at the drill axis, whereby said handpiece guide is rotatable through an angular range of motion equal to said angle when said guide post is engaged within said guide slot.

4. The dental drill guide system of claim 1, comprising a bushing having an axis aligned with said implant axis, said bushing dimensioned to receive a drill.

5. The dental drill guide system of claim 1, wherein said handpiece guide comprises a curved, partially annular member.

6. The dental drill guide system of claim 1, wherein said handpiece guide comprises first and second handpiece guide portions fittable to one another about at least a portion of the handpiece.

7. A dental drill guide system for use with an existing dental handpiece, comprising:
   a base adapted to fit conformingly over at least a portion of a patient's dentition, said base including a surgical guide with a guide receptacle, said guide receptacle including an arcuate-shaped guide slot, at least a portion of the guide receptacle extending outwardly from an outer surface of the base, wherein said surgical guide comprises at least one bushing having an axis that is alignable with the drill axis, said bushing being sized to cooperate with said drill, whereby said bushing constrains lateral translation of the drill axis when said drill is engaged with said bushing; and
   a handpiece guide attachable to the dental handpiece, said handpiece guide including a guide post extending perpendicularly from the handpiece guide and engagable with said guide slot, said guide post of said handpiece guide aligned parallel to, and offset with respect to, a drill axis of a drill, said guide post being longitudinally slidable through the arcuately-shaped guide slot, and wherein said handpiece is rotatable about the drill axis and longitudinally movable along the drill axis with said handpiece guide engaged with said guide slot.

8. The dental drill guide system of claim 1, wherein said arcuate-shaped slot defines a first endpoint and a second endpoint defining an angle formed between the first endpoint and the second endpoint with respect to the drill axis, whereby said handpiece guide is rotatable through an angular range of motion equal to the angle when said guide post is engaged with said guide slot.

9. The dental drill guide system of claim 7, wherein said bushing is removably received within said base of said drill guide.

10. A dental drill guide system for use with an existing dental handpiece, comprising:
    a surgical guide including a substantially semi-cylindrically shaped guide receptacle having a lateral opening and a stop wall; and
    a handpiece guide attachable to the dental handpiece, said handpiece guide receivable within said guide receptacle and engageable with said stop wall to limit a drill depth of the dental handpiece, wherein said handpiece guide comprises a curved, partially annular member removably attached to the dental handpiece;

wherein said handpiece guide comprises a first handpiece guide portion and a second handpiece guide portion, said handpiece guide being shaped to cooperate with said dental handpiece to limit a drill depth of said handpiece, and wherein said first handpiece guide portion defining a locking mechanism with a female clip portion and a male clip portion adapted to cooperate with said female clip portion to couple said first handpiece guide portion with said second handpiece guide portion.

11. The dental drill guide system of claim 10, in combination with a drill defining a drill axis, said guide receptacle defining a guide axis, wherein the drill axis is substantially aligned with said guide axis when said handpiece guide is received within said guide receptacle.

12. The dental drill guide system of claim 10, wherein said handpiece guide further comprises a hinge rotatably joining said first handpiece guide portion and said second handpiece guide portion.

\* \* \* \* \*

UNITED STATES PATENT AND TRADEMARK OFFICE
CERTIFICATE OF CORRECTION

PATENT NO. : 8,585,402 B2  
APPLICATION NO. : 12/548195  
DATED : November 19, 2013  
INVENTOR(S) : Vogel et al.

Page 1 of 1

It is certified that error appears in the above-identified patent and that said Letters Patent is hereby corrected as shown below:

In the Claims

In column 10, line 51, in Claim 8, delete "claim 1" and insert --claim 7--, therefor Signed and Sealed this
Twenty-second Day of April, 2014

Michelle K. Lee
*Deputy Director of the United States Patent and Trademark Office*